United States Patent [19]
Todd et al.

[11] Patent Number: 5,358,481
[45] Date of Patent: Oct. 25, 1994

[54] APPARATUS AND METHODS FOR CONTROLLING MIXTURES OF BLOOD AND CARDIOPLEGIA

[75] Inventors: Robert J. Todd; Kevin G. Marcus, both of Salt Lake City, Utah

[73] Assignee: Research Medical, Inc., Salt Lake City, Utah

[21] Appl. No.: 71,692

[22] Filed: Jun. 3, 1993

[51] Int. Cl.$^5$ .......................................... A61M 37/00
[52] U.S. Cl. .......................................... 604/4; 604/9; 604/52; 422/44
[58] Field of Search .................... 604/4, 5, 8, 9, 29, 604/52, 93, 175, 236, 256; 422/44

[56] References Cited

U.S. PATENT DOCUMENTS

| | | | |
|---|---|---|---|
| 4,257,416 | 3/1981 | Prager | 602/52 |
| 4,416,280 | 11/1983 | Carpenter et al. | 604/56 |
| 4,701,159 | 10/1987 | Brown et al. | 604/175 |
| 5,221,255 | 6/1993 | Mahurkar et al. | 604/282 |
| 5,271,410 | 12/1993 | Wolzinger et al. | 128/692 |
| 5,322,500 | 6/1994 | Johnson et al. | 604/30 |

Primary Examiner—Paul Prebilic
Attorney, Agent, or Firm—Workman, Nydegger and Jensen

[57] ABSTRACT

Methods and apparatus are disclosed for variably controlling the ratio of blood to cardioplegia solution to be administered to a patient. A presently preferred embodiment of the apparatus of the invention comprises a multilumen tubing member having a blood supply lumen and three cardioplegia supply lumens, each having approximately the same tubing wall thickness, but having different inside diameters so that causing flow through different combinations of the cardioplegia lumens will result in different ratios of blood to cardioplegia. The four tubes comprising the multilumen tubing member are advantageously connected by web members, thereby facilitating use with a roller pump and minimizing the tangle of tubes.

17 Claims, 2 Drawing Sheets

APPARATUS AND METHODS FOR CONTROLLING MIXTURES OF BLOOD AND CARDIOPLEGIA

BACKGROUND OF THE INVENTION

1. Technical Field

The present invention is directed to apparatus used in the administration of blood and cardioplegia solution during cardiac surgery.

2. Background Information

Since the early days of cardiac surgery, it has been recognized that in order to provide the optimum surgical conditions when operating on the heart, it is necessary to interrupt the normal operation of the heart. For obvious reasons, an arrested, flaccid heart is preferred during a cardiac surgical procedure over a beating heart with blood flowing through it. Thus, in order to be able to efficiently perform cardiac surgery, it is often necessary to use cardiopulmonary-bypass techniques and to isolate the heart from its life-giving blood supply.

It has been found that many deaths occurring after cardiac surgery are due to acute cardiac failure. At first, it was believed that the heart was simply beyond repair and that the operation had failed to correct the problem. Later, it was discovered that many of these postoperative deaths were due to new, and often extensive, perioperative (during or within 24 hours after the surgical procedure) myocardial necrosis (death of the heart tissue). Furthermore, many patients who survived were found to have suffered myocardial necrosis to a significant degree, thereby resulting in low cardiac blood output.

It is now known that myocardial necrosis occurs because the energy supply or reserve of the cardiac muscle cells is inadequate to supply the needs of the heart. The availability of oxygen dramatically affects the cell's ability to satisfy these energy requirements. For example, anaerobic metabolism of glucose produces two (2) moles of adenosine triphosphate ("ATP") per mole of glucose (as well as harmful acid metabolites), whereas aerobic metabolism of glucose produces thirty-six (36) moles of ATP per mole of glucose. Therefore, one of the primary goals of myocardial preservation techniques during surgery is to reduce myocardial oxygen consumption.

Myocardial oxygen consumption is significantly reduced by stopping the electromechanical work of the heart. The oxygen demands of the beating empty heart at 37° C. are four to five times those of the arrested heart (i.e., 4–5 ml/100-gm/min compared with 1 ml/100-gm/min). Buckberg, G. D., "Strategies and Logic of Cardioplegic Delivery to Prevent, Avoid, and Reverse Ischemic and Reperfusion Damage," 93 *The Journal of Thoracic and Cardiovascular Surgery*, 127, 136 (January 1987) (hereinafter referred to as: Buckberg, "Strategies and Logic of Cardioplegic Delivery").

The normal heart receives its blood supply through the left and right coronary arteries which branch directly from the aorta. Generally, the veins draining the heart flow into the coronary sinus which empties directly into the right atrium. A few veins, known as thesbian veins, open directly into the atria or ventricles of the heart.

One of the early methods utilized to protect the myocardium during surgery was normothermic perfusion of the empty beating heart. This method was utilized in an effort to maintain the heart, as nearly as possible, in normal conditions during surgery. Although the procedure eliminated the problem of blood flow, dissection and suturing were still difficult to perform because of the firmness of the myocardium and the beating of the heart. Additionally, it was found that a significant amount of damage still occurred to the myocardium even when this procedure was utilized.

A second method which was developed to protect the myocardium was intermittent cardiac ischemia with moderate cardiac hypothermia. This method requires that the entire body be perfused at a temperature of from 28° C. to 32° C., thus slowing all bodily functions, including those of the heart. The heart is fibrillated before aortic cross-clamping to stop the beating. The surgeon can then operate for approximately fifteen to twenty-five minutes, after which time the heart beat is necessarily resumed for three to five minutes. This procedure proved to be an inefficient method for performing operations and had many attendant dangers, not the least of which is subjecting the heart to multiple fibrillations.

A third method which has been utilized is profound hypothermic cardiac ischemia. This method requires that the temperature of the heart be lowered to about 22° C. by the infusion of a cooled perfusate and/or by filling the pericardium with cold saline solution. One of the major disadvantages of this technique is that the heart continues to fibrillate, exhausting the heart's stored energy. As a result, the heart becomes acidotic, which over time causes irreversible muscle damage.

A fourth method which has been developed to preserve the myocardium during surgery is the infusion of a cold cardioplegic fluid to cool and stop the beating of the heart. After the initial infusion, the heart is reperfused approximately every thirty (30) minutes to maintain the cool, dormant state of the heart.

Cardioplegia, which literally means "heart stop," has proved quite advantageous. Cardioplegic solutions, typically containing potassium, magnesium procaine, or a hypocalcemic solution, stop the heart by depolarizing cell membranes. Cardioplegia may be administered in an antegrade manner (through arteries in the normal direction of blood flow), in a retrograde manner (through veins opposite the normal blood flow direction), or in a combination of retrograde and antegrade administration.

The most recent method for preserving the myocardium during surgery utilizes continuous warm blood cardioplegia. Warm oxygenated blood cardioplegia has certain theoretical advantages over cold cardioplegia, such as continuously supplying oxygen and substrates to the arrested heart while avoiding the side effects of hypothermia. Salerno, Thomas A. et. al., "Retrograde Continuous Warm Blood Cardioplegia: A New Concept in Myocardial Protection" 51 *Annual of Thoracic Surgery* 245 (1991).

The use of warm blood cardioplegia to protect the myocardium has proven the most advantageous method of those used to date. Warm blood cardioplegia satisfies the myocardial metabolic demands of the arrested heart by providing warm blood with oxygen contents that exceed 15 ml of oxygen for every 100 ml of blood.

Studies reveal that functional recovery is significantly improved when warm blood cardioplegic solution is used. A study by Magovern and co-workers reveals that oxygen delivery at temperatures above 20° C. is significantly improved over lower temperatures.

Engleman, Richard M., "Retrograde Continuous Warm-blood cardioplegia," 51 *Annual of Thoracic Surgery* 180 (1991). Cardioplegia may be induced immediately after extracorporeal circulation has begun, provided that the pulmonary artery is collapsed to attest to the adequacy of venous return.

Warm-blood cardioplegia is often initiated by placing an aortic antegrade cardioplegia cannula followed by the placement of a retrograde coronary sinus catheter. Typically, a high-potassium (50 mEq KCl) warmblood cardioplegic solution is infused through the antegrade cannula to rapidly induce cardiac arrest. Following diastolic arrest, it is typical to switch perfusion from a bag containing the high-potassium cardioplegic solution to a bag containing a low-potassium (30 mEq KCl) solution, which is infused continuously. Reducing the amount of potassium perfused into the heart lessens the risk of overloading the heart tissues with potassium, which overload makes it more difficult to restart the heart after surgery. Overload of potassium could also result in ischemic periods in the heart muscles, or cause other problems following surgery.

Although the use of high-potassium cardioplegic solution to arrest the heart followed by use of a low-potassium solution is widely practiced, as the best method presently available, it is known that this practice is not altogether satisfactory. In order to insure that enough potassium is administered to maintain a state of heart stasis, the low-potassium solution still introduces too much potassium for many patients. This causes the problems mentioned above, and further results in the administration of a higher volume of fluids than necessary if one were to have better control over the amount of potassium solution infused into the patient. Excess infusion of liquids forces the patient's renal system to work harder to restore equilibrium, which can be an unreasonable strain to a patient as ill as those typically requiring open heart surgery.

SUMMARY OF THE INVENTION

It is a primary object of the present invention to provide methods and apparatus which permit variable control of the ratio of blood to cardioplegia solution during the course of a surgical procedure without requiring the use of different solutions of cardioplegia solution.

Another object of the present invention is to provide methods and apparatus permitting reduction of the amount of potassium or other active constituent of cardioplegia solution, to the lowest level required at different stages of a surgical procedure requiring heart stasis.

Yet another object of the present invention is to provide methods and apparatus which decrease the amount of fluids administered during the course of cardioplegia.

These and other objects and advantages of the invention will be better understood by reference to the detailed description, or will be appreciated by the practice of the invention.

To achieve the foregoing objects, and in accordance with the invention as embodied and broadly described herein, the apparatus of the invention comprises blood tubing means for carrying blood for infusion into a patient and cardioplegia tubing means including a plurality (preferably three), of cardioplegia supply tubes for carrying cardioplegia solution for infusion into a patient.

Each of the cardioplegia supply tubes are provided with valve means for controlling the flow of cardioplegia solution between the source of cardioplegia solution and the patient. Each valve means has at least two positions: a first position which permits administration of cardioplegia solution to the patient, and a second position which prevents such administration. Preferably, the cardioplegia solution is returned to the source thereof when the valve means is in the second position so that a conventional roller pump may be used to pump blood through the blood tubing means and cardioplegia solution through the cardioplegia tubing means without causing overpressure to develop.

Appropriate positioning of the valve means in the first of second positions permits variable control of the ratio of blood to cardioplegia, since more or less cardioplegia will be infused with the blood depending upon the combination of valve positions selected.

BRIEF DESCRIPTION OF THE DRAWINGS

In the accompanying drawings, which represent the best mode presently contemplated for carrying out the present invention.

DETAILED DESCRIPTION OF THE PREFERRED EMBODIMENT

The present invention is directed to methods and apparatus for use in the administration of blood and cardioplegia solution. More specifically, the present invention is directed to methods and apparatus useful for variably controlling the ratio of blood to cardioplegia solution so that different ratios of blood to cardioplegia solution may be employed during the course of a surgical procedure. Such methods and apparatus are useful in minimizing problems due to the over administration of cardioplegia solution by making it an easy matter to reduce the amount of cardioplegia solution used at different stages of a surgical procedure. Practice of the present invention also reduces the amount of liquids added to a patient's circulatory system during surgery, and has the added advantage of increasing the relative amount of blood administered during cardioplegia, since a higher ratio of blood to cardioplegia solution will typically be obtainable in connection with the practice of the present invention than when using conventional procedures.

Figure 1:
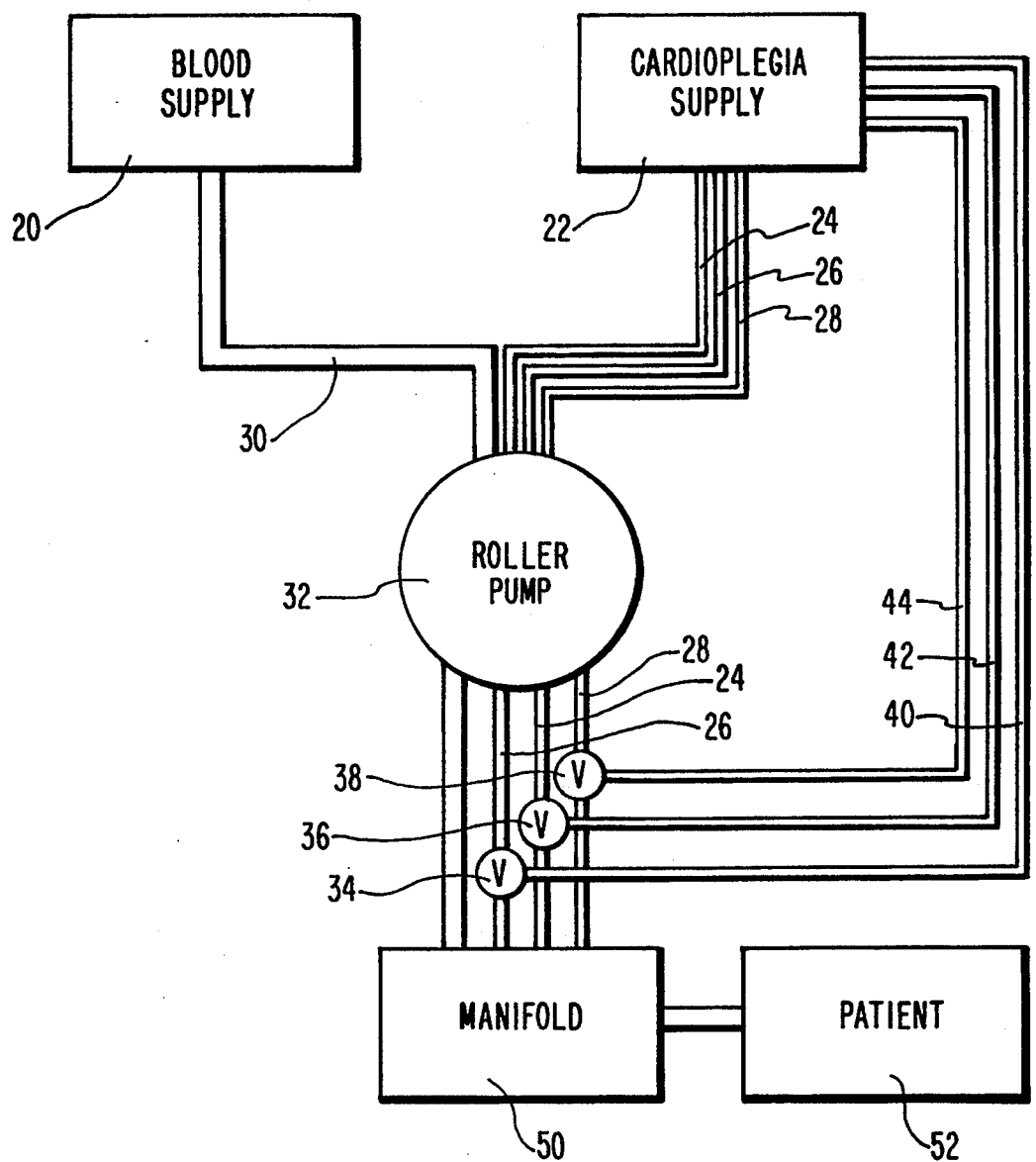
FIG. 1 is a block diagram which illustrates the relationship of the general components of the presently preferred apparatus of the present invention.

A block diagram useful for better understanding and appreciating the basic concepts of the present invention is set forth in FIG. 1. Cardioplegia requires both a blood supply and a supply of cardioplegia solution. The block identified by reference numeral 20 in FIG. 1 is used to represent a supply or source of blood for use during cardioplegia. Suitable blood sources include bagged blood or blood collected from the patient and treated for reinfusion into the patient. The latter approach, sometimes called autotransfusion, is generally preferred because it avoids incompatibility problems which sometimes can occur when providing transfusions of blood obtained from someone other than the patient. Use of a patient's own blood during cardioplegia has also become increasingly important in view of issues relating to the safety of replacement blood, such as the current prevalence of acquired immune deficiency syndrome (AIDS) or other diseases among blood donors in some locales.

Cardioplegia solution is most conveniently supplied in a bag which may be hung in a conventional fashion. Block 22 represents a source or supply of cardioplegia solution. For purposes of simplicity and brevity, the following discussion shall presume the cardioplegia solution employs potassium to effect diastolic arrest. Nevertheless, it should be understood that any suitable cardioplegia solution could be substituted for the potassium solution specifically mentioned.

In conventional cardioplegia systems, it has been common to prepare two different cardioplegia solutions, as noted above in the background section. At the onset of cardioplegia in these systems, a cardioplegia solution containing a relatively high concentration of potassium (e.g., 50 mEq KCl) is typically used to rapidly effect diastolic arrest. Then, the concentrated source of cardioplegia solution is removed and replaced by cardioplegia solution having a reduced concentration of potassium (e.g., 30 mEq KCl). This process of changing bags of cardioplegia solution at different stages of the surgical procedure is greatly preferable to continuing the use of a high potassium cardioplegia solution but is much too cumbersome for controlling an optimum amount of potassium introduced to a specific patient during the course of surgery. In accordance with the present invention, it is vastly preferable to be able to easily alter the amount of potassium, upwardly or downwardly as may be required, so as to introduce the minimum amount of potassium necessary to maintain diastolic arrest.

This is advantageously accomplished by providing cardioplegia tubing means for carrying cardioplegia solution from the source of cardioplegia solution for infusion into a patient, which cardioplegia tubing means comprises a plurality of cardioplegia supply tubes rather than a single tube as might be used in conventional cardioplegia setups.

FIG. 1 illustrates the use of three cardioplegia supply tubes 24, 26 and 28, which serve as cardioplegia tubing means. It is presently preferred that three tubes be used as the cardioplegia tubing means for carrying cardioplegia solution, although it should be understood that two tubes could be employed in place of three, or more than three tubes could be used. Each of the cardioplegia supply tubes is advantageously made of a suitable grade of medical grade plastic, although it should also be understood that structures other than plastic tubing could be used as cardioplegia tubing means, bearing in mind that the function of the tubing means is to carry cardioplegia solution.

In accordance with the presently preferred embodiment of the invention, these three tubes are fed into suitable means for pumping blood and cardioplegia solution. In FIG. 1, the cardioplegia supply tubes are fed into a pump 32 together with a blood supply tube 30, said blood supply tube serving as blood tubing means for carrying blood from the source of blood for infusion into a patient. It is preferred that the pump be a conventional roller pump. Roller pumps are generally preferred when pumping blood and related solutions because such pumps do not directly contact the blood, thereby maintaining sterility without the need for cleansing between uses. Roller pumps are also gentle on blood, thereby avoiding damage to blood cells. They are also easily adjustable so as to provide a variable but precise flow of blood. A typical roller pump has a hemispherical member configured so as to accept medical tubing, and a two-headed arm which rotates so as to alternately contact the inlet end of the tubing and then advance blood or other fluid through to the outlet end of the tubing as one head and then the other rotates.

In accordance with the present invention, each of cardioplegia supply tubes 24, 26 and 28 are provided with respective valve means 34, 36 and 38 for controlling the flow of cardioplegia solution between the source of cardioplegia solution and the patient. No valve is required for the blood supply tube 30, the flow of blood being controlled by operation of the roller pump.

Suitable valve means have two or more positions. A first position permits administration of cardioplegia solution to the patient, while a second position stops flow to the patient. However, were the second position to simply block the flow of cardioplegia solution, the continued operation of the roller pump 32 would cause pressure to build up within the associated cardioplegia tubes until the tubing or connections would burst.

Accordingly, return tubing means 40, 42 and 44 are provided to carry cardioplegia solution back to the cardioplegia supply 22. Alternatively, the return tubing can be connected to cardioplegia tubes 24, 26 and 28. Other arrangements of tubing could also be utilized as will be readily understood by one of ordinary skill after reviewing the teachings herein. When the valve means is in the second position, cardioplegia solution is recycled for reuse.

It is possible to select different combinations of valve positions. For example, it is possible to place all three valves in the second position, so that no cardioplegia solution is administered to the patient. It is possible to place all three valves in the first position so that a relatively high flow of cardioplegia solution occurs. Other combinations of valve positions provide intermediate amounts of cardioplegia solution. It will be appreciated that selection of which valves are placed in the first position controls how much cardioplegia solution is delivered to the patient. Since only a single blood tube is used regardless of how many cardioplegia tubes are used, it will be appreciated that operation of valves 34, 36 and 38 in different combinations provide different ratios of blood to cardioplegia solution.

Roller pump 32 operates in conventional fashion in a manner well known to those skilled in the art. By way of summary, a rotor is moved in a rolling motion across tubing, which is supported by a roller pump support member. The rolling motion of the rotor compresses the tubing against the support member, thereby pushing fluid ahead of the rotor.

When using a roller pump, it is important that each tube 24, 26, 28 and 30 have the same wall thickness, thereby insuring that each tube is fully occluded during operation of the rotor. Each tube should also be constructed of a material having a durometer soft enough to permit occlusion during operation of the roller pump. For example, small diameter cardioplegia tubing having a durometer of 68 is generally too hard for convenient use in conventional roller pumps, whereas a durometer of about 60 is more easily used. Blood supply tube 30, being larger in diameter, may nevertheless use the conventional durometer of 68.

It is not necessary that the inside diameter of each tube be the same. It is a feature of the invention to provide a broad range of ratios of cardioplegia solution to blood by providing cardioplegia tubes having a variety of inside diameters. Although it will be appreciated that a wide variety of combinations of tubing diameters could be selected, the presently preferred combinations are set forth in Table 1, in which arbitrary designations A, B, C and D are used for ease in making reference to the various tubes:

TABLE 1

| Tube | Description | Inside Diameter |
| --- | --- | --- |
| A | Blood supply tube | 0.25 inches |
| B | Cardioplegia tube | 0.088 inches |
| C | Cardioplegia tube | 0.072 inches |
| D | Cardioplegia tube | 0.056 inches |

The use of tubes A, B, C and D having the inside diameters as set forth in Table 1 give rise to seven useful combinations of blood and cardioplegia of varying ratios of cardioplegia to blood, as set forth in Table 2 (rounded off to the nearest whole number):

TABLE 2

| Combination | Ratio of Cardioplegia to Blood |
| --- | --- |
| ABCD | 1:4 |
| ABC | 1:5 |
| ABD | 1:6 |
| ACD | 1:7 |
| AB | 1:8 |
| AC | 1:12 |
| AD | 1:20 |

Among these ratios, 1:4, 1:8, 1:12 and 1:20 appear to be the most likely to be used during typical procedures, it being particularly desirable to provide ratios of 1:4, 1:8, between about 1:10 and 1:15, and between about 1:15 and 1:20.

It will be appreciated that valves 34, 36 and 38 could be labeled and a reference card provided to instruct a physician's assistant or perfusionist regarding the positions of the valves necessary to obtain a desired ratio of blood to cardioplegia. Alternatively, it is possible to provide an electronic module having a multiposition switch corresponding to the ratios available, together with internal servo-controlled valves which would select/deselect the appropriate valves in order to provide the corresponding ratio of blood to cardioplegia. In light of the teachings herein, other useful means for setting the valves to the first or second positions in order to obtain a desired ratio of blood to cardioplegia will be readily appreciated.

Figure 2:
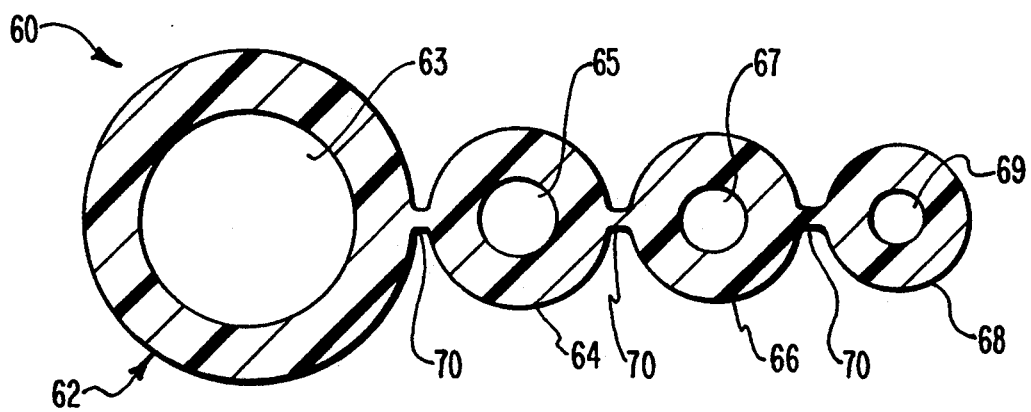
FIG. 2 is a sectional view of a multilumen tube presently preferred for use in the practice of the present invention.

Although traditional plastic tubing could be used as tubes 24, 26, 28 and 30, this requires some care in placing them into the roller pump. The use of four tubes also adds to the plethora of tubes used for various purposes when accomplishing cardiac surgery. Accordingly, it is preferred that the tubes be connected so as to form a multilumen tubing member, such as illustrated in FIG. 2, where a presently preferred form of a multilumen tubing member 60 is comprised of a blood lumen tube 62 having a blood lumen 63, and a plurality of cardioplegia lumen tubes 64, 66 and 68 having cardioplegia lumens 65, 67 and 69, respectively. Advantageously, the blood and cardioplegia tubes are secured together by webs 70 which serve as means for securing the blood tube and the cardioplegia tubes in a substantially planar spaced relationship. This construction reduces the tangle of tubes and can simplify the task of fitting them into a roller pump.

It is generally preferred that blood and cardioplegia solution be joined before infusion into a patient, such as by introducing them into a manifold 50. Suitable manifolds might be as simple as a chamber having multi-input lines to accommodate each cardioplegia tube and the blood tube, and a single output line. Other suitable manifolds could incorporate more complex designs for joining the blood and cardioplegia solution prior to infusion. The output from manifold 50, containing joined blood and cardioplegia solution, is finally infused into a patient 52 in conventional fashion.

In many instances, it is desirable to carefully control the temperature of the blood and cardioplegia solution being administered. It should be understood that a heat exchanger can be incorporated into the system described above without departing from the inventive teachings set forth herein.

Figure 3:
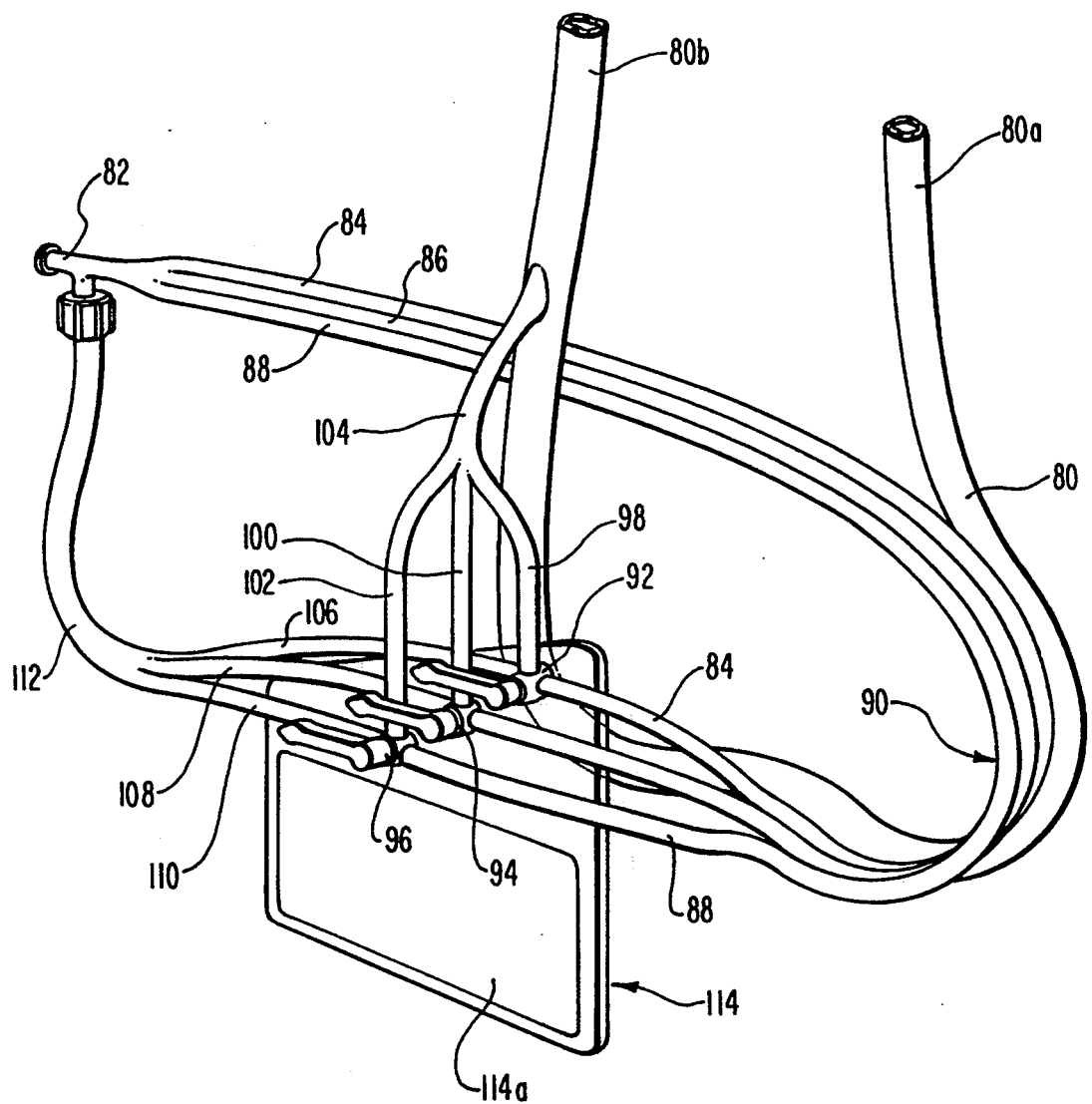
FIG. 3 is a perspective view of a presently preferred embodiment of a multilumen tubing member apparatus for use in the administration of blood and cardioplegia solution to a patient.

FIG. 3 illustrates portions of a presently preferred multilumen tubing member apparatus for use in the administration of blood and cardioplegia solution. A blood supply tube 80 is attached at first end 80a to a source of blood (not shown). A source of cardioplegia solution (not shown) is connected to a fitting 82. Fitting 82 is connected to three cardioplegia tubes 84, 86, and 88. The cardioplegia tubes and blood supply tube 80 are brought together for placement into a roller pump, which is not shown, but which would be placed in the vicinity of the curve identified with the reference numeral 90.

Utilizing this setup, a roller pump would be operated so as to draw blood within blood supply tube 80 from point 80a, and within cardioplegia tubes 84, 86, and 88 from fitting 82. Cardioplegia solution would next be pumped through two position valves 92, 94, and 96 associated with tubes 84, 86, and 88, respectively. In one position of valves 92, 94, and 96, cardioplegia solution would be passed through tubes 98, 100, and 102, respectively, which tubes are advantageously joined together into tube 104, and then joined with blood tube 80 for infusion into a patient through end 80b and then through a catheter or other infusion device (not shown).

In the other position, valves 92, 94, and 96 pass cardioplegia solution from tubes 84, 86, and 88 to tubes 106, 108, and 110, which are thereafter joined into tube 112. Tube 112 is advantageously connected to fitting 82, so that returning cardioplegia solution may be recirculated into tubes 84, 86, and 88 without building up backpressure in the cardioplegia tubing.

A card element 114 is useful for securing valves 92, 94, and 96 and providing support to the multilumen tubing member apparatus. Card element also provides a convenient surface 114a upon which to print the desired orientation of valves 92, 94, and 96 in order to obtain the various ratios of blood to cardioplegia solution which are available in a particular situation.

It should be noted that each rotation of the roller pump will result in a flow of a measured amount of blood, but the amount of cardioplegia solution pumped is dependent upon the position of valves 92, 94, and 96. Hence, valves 92, 94, and 96 may be positioned so that no cardioplegia solution is introduced through tube 104 into the blood flow through tube 80. As one or more valves are oriented to the other position wherein cardioplegia solution is caused to flow to the patient, the volume of fluid infused into the patient per minute is increased.

In some circumstances, a physician will prefer to maintain a constant flow of blood per minute into the patient, even though the overall flow of fluid increases. In other circumstances, the physician may prefer to maintain a constant flow of fluid into the patient, and is less concerned regarding the absolute amount of blood infused. A constant flow of fluid may be obtained by reducing the rate of the roller pump as cardioplegia is added to the blood flow, and increasing the rate of the roller pump as cardioplegia administration is decreased.

From the foregoing discussion, it will appreciated that the present invention makes it possible to control the ratio of blood and cardioplegia solution administered to a patient. The method of the invention involves use of a blood tube for carrying blood and a plurality, preferably three, of cardioplegia tubes for carrying cardioplegia solution. Each of the cardioplegia tubes should be provided with valve means for controlling the flow of cardioplegia solution therethrough, having at least a first position which permits administration of cardioplegia solution to a patient and a second position which results in return of cardioplegia to a source of cardioplegia solution. Blood is pumped through the blood tube and cardioplegia solution is pumped through the cardioplegia solution under the influence of a suitable pump, preferably a roller pump. Depending upon the ratio of blood to cardioplegia desired, the cardioplegia supply tube valve means are placed into the appropriate first or second positions. The overall flow of cardioplegia/blood is controlled by controlling the speed of the pump. Preferably, the separate flows of blood and cardioplegia are then joined together prior to infusion into the patient, such as by use of a manifold.

The present invention provides a significant improvement over conventional approaches for introducing blood and cardioplegia in that a physician now has great control over the amount of cardioplegia administered to a patient. By selecting the appropriate ratio of cardioplegia to blood from time to time during the course of a surgical procedure, it is possible to administer the least amount of potassium necessary to keep the heart in a state of arrest, which is useful both during surgery, and also at the time when it is desired to reestablish normal heart activity following a surgical procedure. Such control is possible even where blood or cardioplegia varies in viscosity from time to time. The present invention also introduces less fluids into the patient since smaller amounts of cardioplegia will typically be administered during the course of most procedures.

It will be appreciated that the present invention may be embodied or utilized in other specific manners or forms without departing from its spirit or essential characteristics. The described embodiments and methods are to be considered in all respects only as illustrative and not restrictive, and the scope of the invention is indicated by the appended claims rather than by the foregoing description. All changes which come within the meaning and range of equivalency of the claims are to be embraced within their scope.

What is claimed and desired to be secured by U.S. Patent is:

1. A system for supplying a variably controlled ratio of blood and cardioplegia solution to a patient, comprising:
   (a) a source of blood;
   (b) a source of cardioplegia solution;
   (c) blood tubing means for carrying a flow of blood from the source of blood for infusion into a patient;
   (d) cardioplegia tubing means for carrying a flow of cardioplegia solution from the source of cardioplegia solution for infusion into the patient, said cardioplegia tubing means comprising a plurality of cardioplegia supply tubes;
   (e) a plurality valve means each of which is associated with each of the plurality of cardioplegia tubes for controlling the flow of cardioplegia solution between the source of cardioplegia solution and the patient, said valve means having a first position which permits administration of cardioplegia solution to a patient and a second position which results in recirculation of cardioplegia solution so that selection of the first or second positions of said valve means results in a plurality of different ratios of blood to cardioplegia solution; and
   (f) pump means for pumping blood and cardioplegia solution.

2. A system for supplying a variably controlled ratio of blood and cardioplegia solution as defined in claim 1, further comprising means for joining the flow of blood and cardioplegia solution together for administration to the patient.

3. A system for supplying a variably controlled ratio of blood and cardioplegia solution as defined in claim 1 wherein the cardioplegia tubing means comprises three cardioplegia supply tubes.

4. A system for supplying a variably controlled ratio of blood and cardioplegia solution as defined in claim 1 wherein the pump means is a roller pump.

5. A system for supplying a variably controlled ratio of blood and cardioplegia solution as defined in claim 1 providing a plurality of different ratios of blood to cardioplegia controlled by operation of the plurality of valve means between the first and second positions, wherein the plurality of ratios of blood to cardioplegia which are available include ratios of about 4 to 1, about 8 to 1, between about 10 to 1 and about 15 to 1, and between about 15 to 1 and about 20 to 1.

6. A system for supplying a variably controlled ratio of blood and cardioplegia solution as defined in claim 1 providing a plurality of different ratios of blood to cardioplegia controlled by operation of the plurality of valve means between the first and second positions, wherein the plurality of ratios of blood to cardioplegia which are available include ratios of about 4 to 1, about 5 to 1, about 6 to 1, about 7 to 1, about 8 to 1, about 12 to 1, and about 20 to 1.

7. A system for supplying a variably controlled ratio of blood and cardioplegia solution as defined in claim 4 wherein the cardioplegia tubing means comprises three cardioplegia supply tubes.

8. A system for supplying a variably controlled ratio of blood and cardioplegia solution as defined in claim 7 wherein
   the blood tubing means comprises a blood supply tube having an inside diameter of about 0.25 inches;
   the cardioplegia supply tubes have inside diameters of about 0.088 inches, 0.072 inches and 0.056 inches, respectively; and
   the blood supply tube and the cardioplegia supply tubes all have substantially the same wall thickness.

9. A system for supplying a variably controlled ratio of blood and cardioplegia solution as defined in claim 8, further comprising means for joining the flow of blood and cardioplegia solution together for administration to the patient.

10. A system for supplying a variably controlled ratio of blood and cardioplegia solution as defined in claim 1 wherein the cardioplegia tubing means comprises two cardioplegia supply tubes.

11. A system for supplying a variably controlled ratio of blood and cardioplegia solution as defined in claim 4 wherein the cardioplegia tubing means comprises two cardioplegia supply tubes.

12. A system for supplying a variably controlled ratio of blood and cardioplegia solution as defined in claim 4 providing a plurality of different ratios of blood to cardioplegia controlled by operation of the plurality of valve means between the first and second positions, wherein the plurality of ratios of blood to cardioplegia which are available include ratios of about 4 to 1, about 8 to 1, between about 10 to 1 and about 15 to 1, and between about 15 to 1 and about 20 to 1.

13. A system for supplying a variably controlled ratio of blood and cardioplegia solution as defined in claim 4 providing a plurality of different ratios of blood to cardioplegia controlled by operation of the plurality of valve means between the first and second positions, wherein the plurality of ratios of blood to cardioplegia which are available include ratios of about 4 to 1, about 5 to 1, about 6 to 1, about 7 to 1, about 8 to 1, about 12 to 1, and about 20 to 1.

14. A system for supplying a variably controlled ratio of blood and cardioplegia solution as defined in claim 1 providing a plurality of different ratios of blood to cardioplegia controlled by operation of the plurality of valve means between the first and second positions, wherein the plurality of ratios of blood to cardioplegia which are available include ratios of about 4 to 1 and about 8 to 1.

15. A system for supplying a variably controlled ratio of blood and cardioplegia solution as defined in claim 4 providing a plurality of different ratios of blood to cardioplegia controlled by operation of the plurality of valve means between the first and second positions, wherein the plurality of ratios of blood to cardioplegia which are available include ratios of about 4 to 1 and about 8 to 1.

16. A system for supplying a variably controlled ratio of blood and cardioplegia solution as defined in claim 4 further comprising web means for securing the blood tubing means and the plurality of cardioplegia supply tubes together in a substantially planar spaced relationship in the portion placed within the roller pump.

17. A system for supplying a variably controlled ratio of blood and cardioplegia solution as defined in claim 4, wherein each of the blood tubing means and the plurality of cardioplegia supply tubes have the same wall thickness.

* * * * *